(12) United States Patent
Watson et al.

(10) Patent No.: US 8,290,730 B2
(45) Date of Patent: Oct. 16, 2012

(54) SYSTEMS AND METHODS FOR ASSESSING MEASUREMENTS IN PHYSIOLOGICAL MONITORING DEVICES

(75) Inventors: James N. Watson, Dunfermline (GB); Clark R. Baker, Jr., Newman, CA (US); Paul Stanley Addison, Edinburgh (GB)

(73) Assignee: Nellcor Puritan Bennett Ireland, Galway (IE)

( * ) Notice: Subject to any disclaimer, the term of this patent is extended or adjusted under 35 U.S.C. 154(b) by 540 days.

(21) Appl. No.: 12/494,971

(22) Filed: Jun. 30, 2009

(65) Prior Publication Data
US 2010/0332173 A1    Dec. 30, 2010

(51) Int. Cl.
G06F 17/00    (2006.01)
G06F 17/40    (2006.01)

(52) U.S. Cl. ............................. 702/85; 702/19; 600/301
(58) Field of Classification Search .................... 702/85, 702/19, 50, 98, 100, 139
See application file for complete search history.

(56) References Cited

U.S. PATENT DOCUMENTS

| | | | |
|---|---|---|---|
| 3,835,840 A | 9/1974 | Mount | |
| 4,561,447 A | 12/1985 | Kawamura et al. | |
| 4,676,253 A | 6/1987 | Newman et al. | |
| 4,729,382 A | 3/1988 | Schaffer et al. | |
| 4,800,495 A | 1/1989 | Smith | |
| 4,807,631 A | 2/1989 | Hersh et al. | |
| 4,824,242 A | 4/1989 | Frick et al. | |
| 4,830,017 A | 5/1989 | Perry et al. | |
| 4,836,213 A | 6/1989 | Wenzel et al. | |
| 4,854,327 A | 8/1989 | Kunig | |
| 4,859,057 A | 8/1989 | Taylor et al. | |
| 4,863,265 A | 9/1989 | Flower et al. | |
| 4,869,254 A | 9/1989 | Stone et al. | |
| 4,883,353 A | 11/1989 | Hausman et al. | |
| 4,898,176 A | 2/1990 | Petre | |
| 4,901,238 A | 2/1990 | Suzuki et al. | |
| 4,924,871 A | 5/1990 | Honeyager | |
| 4,928,700 A | 5/1990 | Harada | |
| 4,951,679 A | 8/1990 | Harada | |
| 4,960,126 A | 10/1990 | Conlon et al. | |
| 4,976,268 A | 12/1990 | Kurosawa et al. | |
| 4,987,900 A | 1/1991 | Eckerle et al. | |
| 5,025,791 A | 6/1991 | Niwa | |
| 5,065,765 A | 11/1991 | Eckerle et al. | |
| 5,078,136 A | 1/1992 | Stone et al. | |

(Continued)

FOREIGN PATENT DOCUMENTS
EP    0443267    8/1991
(Continued)

OTHER PUBLICATIONS

International Search Report PCT/US2010/038108, 4 pages, mailed Oct. 19, 2010.

(Continued)

*Primary Examiner* — Hal Wachsman

(57) ABSTRACT

Methods and systems are provided for deriving and analyzing shape metrics, including skewness metrics, from physiological signals and their derivatives to determine measurement quality, patient status and operating conditions of a physiological measurement device. Such determinations may be used for any number of functions, including indicating to a patient or care provider that the measurement quality is low or unacceptable, alerting a patient or care provider to a change in patient status, triggering or delaying a recalibration of a monitoring device, and adjusting the operating parameters of a monitoring system.

20 Claims, 6 Drawing Sheets

U.S. PATENT DOCUMENTS

| | | | |
|---|---|---|---|
| 5,099,841 A | 3/1992 | Heinonen et al. |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada et al. |
| 5,163,328 A | 11/1992 | Holland et al. |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,190,038 A | 3/1993 | Polson et al. |
| 5,204,922 A | 4/1993 | Weir et al. |
| 5,238,000 A | 8/1993 | Niwa |
| 5,241,964 A | 9/1993 | McQuilkin |
| 5,255,686 A | 10/1993 | Takeda et al. |
| 5,269,312 A | 12/1993 | Kawamura et al. |
| 5,289,823 A | 3/1994 | Eckerle |
| 5,299,120 A | 3/1994 | Kaestle |
| 5,309,917 A | 5/1994 | Wang et al. |
| 5,349,519 A | 9/1994 | Kaestle |
| 5,355,882 A | 10/1994 | Ukawa et al. |
| 5,368,026 A | 11/1994 | Swedlow et al. |
| 5,398,680 A | 3/1995 | Polson et al. |
| 5,431,159 A | 7/1995 | Baker et al. |
| 5,450,852 A | 9/1995 | Archibald et al. |
| 5,467,771 A | 11/1995 | Narimatsu et al. |
| 5,485,847 A | 1/1996 | Baker, Jr. |
| 5,490,506 A | 2/1996 | Takatani et al. |
| 5,494,043 A | 2/1996 | O'Sullivan et al. |
| 5,497,779 A | 3/1996 | Takaya et al. |
| 5,505,209 A | 4/1996 | Reining |
| 5,533,511 A | 7/1996 | Kaspari et al. |
| 5,535,753 A | 7/1996 | Petrucelli et al. |
| 5,555,882 A | 9/1996 | Richardson et al. |
| 5,558,096 A | 9/1996 | Palatnik |
| 5,562,621 A | 10/1996 | Claude et al. |
| 5,564,427 A | 10/1996 | Aso et al. |
| 5,575,284 A | 11/1996 | Athan et al. |
| 5,588,425 A | 12/1996 | Sackner et al. |
| 5,595,176 A | 1/1997 | Yamaura |
| 5,617,868 A | 4/1997 | Harada et al. |
| 5,640,964 A | 6/1997 | Archibald et al. |
| 5,649,542 A | 7/1997 | Archibald et al. |
| 5,649,543 A | 7/1997 | Hosaka et al. |
| 5,662,105 A | 9/1997 | Tien |
| 5,662,106 A | 9/1997 | Swedlow et al. |
| 5,676,140 A | 10/1997 | Ukawa et al. |
| 5,682,898 A | 11/1997 | Aung et al. |
| 5,685,316 A | 11/1997 | Schookin et al. |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,743,263 A | 4/1998 | Baker, Jr. |
| 5,743,856 A | 4/1998 | Oka et al. |
| 5,755,669 A | 5/1998 | Ono et al. |
| 5,762,610 A | 6/1998 | Narimatsu et al. |
| 5,766,127 A | 6/1998 | Pologe et al. |
| 5,772,601 A | 6/1998 | Oka et al. |
| 5,772,602 A | 6/1998 | Sakai et al. |
| 5,776,071 A | 7/1998 | Inukai et al. |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,820,550 A | 10/1998 | Polson et al. |
| 5,827,181 A | 10/1998 | Dias et al. |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,853,364 A | 12/1998 | Baker, Jr. |
| 5,857,975 A | 1/1999 | Golub |
| 5,873,834 A | 2/1999 | Yanagi et al. |
| 5,904,654 A | 5/1999 | Wohltmann et al. |
| 5,941,828 A | 8/1999 | Archibald et al. |
| 5,964,711 A | 10/1999 | Voss et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,022,320 A | 2/2000 | Ogura et al. |
| 6,027,452 A | 2/2000 | Flaherty et al. |
| 6,027,453 A | 2/2000 | Miwa et al. |
| 6,027,455 A | 2/2000 | Inukai et al. |
| 6,035,223 A | 3/2000 | Baker, Jr. |
| 6,045,509 A | 4/2000 | Caro et al. |
| 6,067,462 A | 5/2000 | Diab et al. |
| 6,083,157 A | 7/2000 | Noller |
| 6,083,171 A | 7/2000 | Ono et al. |
| 6,083,172 A | 7/2000 | Baker, Jr. |
| 6,094,592 A | 7/2000 | Yorkey et al. |
| 6,095,987 A | 8/2000 | Shmulewitz et al. |
| 6,135,966 A | 10/2000 | Ko |
| 6,157,850 A | 12/2000 | Diab et al. |
| 6,159,157 A | 12/2000 | Archibald et al. |
| 6,161,038 A | 12/2000 | Schookin et al. |
| 6,178,343 B1 | 1/2001 | Bindszus et al. |
| 6,181,959 B1 | 1/2001 | Schollermann et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,292,689 B1 | 9/2001 | Wallace et al. |
| 6,293,915 B1 | 9/2001 | Amano et al. |
| 6,299,582 B1 | 10/2001 | Brockway et al. |
| 6,332,867 B1 | 12/2001 | Chen et al. |
| 6,339,715 B1 | 1/2002 | Bahr et al. |
| 6,350,242 B1 | 2/2002 | Doten et al. |
| 6,371,921 B1 | 4/2002 | Caro et al. |
| 6,393,311 B1 | 5/2002 | Edgar, Jr. et al. |
| 6,411,833 B1 | 6/2002 | Baker, Jr. |
| 6,443,905 B1 | 9/2002 | Nissila et al. |
| 6,453,184 B1 | 9/2002 | Hyogo et al. |
| 6,463,311 B1 | 10/2002 | Diab |
| 6,471,646 B1 | 10/2002 | Thede |
| 6,471,655 B1 | 10/2002 | Baura |
| 6,506,161 B2 | 1/2003 | Brockway et al. |
| 6,514,211 B1 | 2/2003 | Baura |
| 6,519,486 B1 | 2/2003 | Edgar, Jr. et al. |
| 6,524,240 B1 | 2/2003 | Thede |
| 6,561,986 B2 | 5/2003 | Baura et al. |
| 6,564,077 B2 | 5/2003 | Mortara |
| 6,574,491 B2 | 6/2003 | Elghazzawi |
| 6,589,185 B1 | 7/2003 | Archibald et al. |
| 6,594,512 B2 | 7/2003 | Huang |
| 6,600,940 B1 | 7/2003 | Fein et al. |
| 6,602,199 B2 | 8/2003 | Chen et al. |
| 6,602,201 B1 | 8/2003 | Hepp et al. |
| 6,606,511 B1 | 8/2003 | Ali et al. |
| 6,626,839 B2 | 9/2003 | Doten et al. |
| 6,631,281 B1 | 10/2003 | Kastle |
| 6,645,156 B2 | 11/2003 | Oka |
| 6,647,280 B2 | 11/2003 | Bahr et al. |
| 6,650,918 B2 | 11/2003 | Terry |
| 6,658,277 B2 | 12/2003 | Wasserman |
| 6,668,182 B2 | 12/2003 | Hubelbank |
| 6,684,090 B2 | 1/2004 | Ali et al. |
| RE38,476 E | 3/2004 | Diab et al. |
| 6,699,194 B1 | 3/2004 | Diab et al. |
| 6,721,584 B2 | 4/2004 | Baker, Jr. |
| 6,767,328 B2 | 7/2004 | Kulik |
| 6,773,397 B2 | 8/2004 | Kelly |
| 6,783,498 B2 | 8/2004 | Sackner et al. |
| 6,810,277 B2 | 10/2004 | Edgar, Jr. et al. |
| 6,816,741 B2 | 11/2004 | Diab |
| 6,822,564 B2 | 11/2004 | Al-Ali |

| | | |
|---|---|---|
| 6,826,419 B2 | 11/2004 | Diab et al. |
| 6,827,688 B2 | 12/2004 | Goto et al. |
| 6,836,679 B2 | 12/2004 | Baker, Jr. |
| 6,850,787 B2 | 2/2005 | Weber et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,869,403 B2 | 3/2005 | Narimatsu et al. |
| 6,929,610 B2 | 8/2005 | Forstner |
| 6,931,269 B2 | 8/2005 | Terry |
| 6,996,427 B2 | 2/2006 | Ali et al. |
| 7,004,907 B2 | 2/2006 | Banet et al. |
| 7,024,233 B2 | 4/2006 | Ali et al. |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| 7,139,599 B2 | 11/2006 | Terry |
| 7,184,809 B1 | 2/2007 | Sterling et al. |
| 7,215,984 B2 | 5/2007 | Diab et al. |
| 7,215,986 B2 | 5/2007 | Diab et al. |
| 7,252,636 B2 | 8/2007 | Brown |
| 7,320,030 B2 | 1/2008 | Brown |
| 7,335,162 B2 | 2/2008 | Eide |
| 7,373,194 B2 | 5/2008 | Weber et al. |
| 7,376,238 B1 | 5/2008 | Rivas et al. |
| 7,390,300 B2 | 6/2008 | Inukai et al. |
| 7,390,301 B2 | 6/2008 | Skrabal et al. |
| 7,393,327 B2 | 7/2008 | Inukai et al. |
| 7,400,257 B2 | 7/2008 | Rivas |
| 7,455,643 B1 | 11/2008 | Li et al. |
| 7,481,772 B2 | 1/2009 | Banet |
| 7,485,095 B2 | 2/2009 | Shusterman |
| 2001/0053960 A1* | 12/2001 | Lim .................. 702/85 |
| 2002/0128544 A1 | 9/2002 | Diab et al. |
| 2003/0073890 A1* | 4/2003 | Hanna .................. 600/323 |
| 2003/0225337 A1 | 12/2003 | Scharf et al. |
| 2004/0039273 A1 | 2/2004 | Terry |
| 2004/0064020 A1 | 4/2004 | Diab et al. |
| 2004/0133087 A1 | 7/2004 | Ali et al. |
| 2004/0138538 A1 | 7/2004 | Stetson |
| 2004/0138540 A1 | 7/2004 | Baker et al. |
| 2004/0158135 A1 | 8/2004 | Baker et al. |
| 2004/0162493 A1 | 8/2004 | Mills |
| 2004/0171948 A1 | 9/2004 | Terry |
| 2004/0181134 A1 | 9/2004 | Baker et al. |
| 2004/0204637 A1 | 10/2004 | Diab et al. |
| 2005/0004479 A1 | 1/2005 | Townsend et al. |
| 2005/0033129 A1 | 2/2005 | Edgar et al. |
| 2005/0148885 A1 | 7/2005 | Tweed et al. |
| 2005/0251344 A1 | 11/2005 | Appel et al. |
| 2005/0261594 A1 | 11/2005 | Banet |
| 2006/0009700 A1 | 1/2006 | Brumfield et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0200015 A1* | 9/2006 | Baker, Jr. .................. 600/323 |
| 2006/0200016 A1 | 9/2006 | Diab et al. |
| 2006/0206021 A1 | 9/2006 | Diab |
| 2006/0217614 A1 | 9/2006 | Takala et al. |
| 2006/0217628 A1 | 9/2006 | Huiku |
| 2006/0241975 A1 | 10/2006 | Brown |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0073124 A1 | 3/2007 | Li et al. |
| 2007/0083093 A1 | 4/2007 | Diab |
| 2007/0118045 A1 | 5/2007 | Naghavi et al. |
| 2007/0225582 A1 | 9/2007 | Diab et al. |
| 2007/0249467 A1 | 10/2007 | Hong et al. |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0036752 A1 | 2/2008 | Diab et al. |
| 2008/0077022 A1* | 3/2008 | Baker .................. 600/500 |
| 2008/0132798 A1 | 6/2008 | Hong et al. |
| 2008/0146901 A1 | 6/2008 | Katura et al. |
| 2008/0214903 A1 | 9/2008 | Orbach |
| 2008/0214942 A1 | 9/2008 | Oh et al. |
| 2008/0221462 A1* | 9/2008 | Baker .................. 600/485 |
| 2008/0242955 A1 | 10/2008 | Uutela et al. |
| 2009/0048497 A1 | 2/2009 | Keren |
| 2009/0326386 A1 | 12/2009 | Sethi et al. |
| 2009/0326393 A1 | 12/2009 | Sethi et al. |
| 2009/0326395 A1 | 12/2009 | Watson |
| 2010/0016734 A1 | 1/2010 | Sethi et al. |
| 2010/0081940 A1 | 4/2010 | McKenna |

FOREIGN PATENT DOCUMENTS

| | | |
|---|---|---|
| EP | 0755221 | 1/1997 |
| EP | 1195132 A1 | 4/2002 |
| GB | 2 356 250 | 5/2001 |
| GB | 2 356 251 | 5/2001 |
| GB | 2 356 252 | 5/2001 |
| JP | 03-225268 | 10/1991 |
| JP | 03-231630 | 10/1991 |
| JP | 06-142082 | 5/1994 |
| JP | 07-136136 | 5/1995 |
| JP | 25245574 | 9/2005 |
| JP | 26325766 | 12/2006 |
| JP | 27020836 | 2/2007 |
| JP | 3939782 | 7/2007 |
| JP | 27330708 | 12/2007 |
| WO | WO-9843071 | 10/1998 |
| WO | WO-07013708 | 2/2007 |

OTHER PUBLICATIONS

Allen, John and Murray, Alan, "Age-related changes in the characteristics of the photoplethysmographic pulse shape at various body sites," Physiological Measurement, v. 24, pp. 297-307 (2003).

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

Berne, Robert M., Levy, Matthew N., eds., Physiology, 2nd edition, St. Louis, Mosby, 1988, pp. 357-681.

Boshnakov, Georgi, "Some measures for asymmetry of distributions," Statistics & Probability Letters, v. 77, pp. 1111-1116 (2007).

Ferreira, Jose and Steel, Mark, "On Describing Multivariate Skewness: A Directional Approach," Econometrics, 0409010, http://ideas.repec.org/p/wpa/wuwpem/0409010.html, accessed on Aug. 16, 2009.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, CEW, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR ASSESSING MEASUREMENTS IN PHYSIOLOGICAL MONITORING DEVICES

SUMMARY

The present disclosure relates to systems and methods for analyzing physiological signals and, more particularly, the present disclosure relates to systems and methods for deriving and analyzing skewness metrics from physiological signals.

The shape of a physiological signal may hear on both measurement quality and patient status. For example, pulses in a high quality photoplethysmograph (PPG) signal in an oximetry system are often characterized by a sharp downstroke at the beginning of a pulse wave, followed by an upstroke of shorter duration. The time derivative of such a PPG signal is an undulating waveform with both positive and negative parts. The negative parts, corresponding to the sharp downstroke, may reach relatively high values as compared to the magnitude of the positive parts corresponding to the more gradual upstroke. The characteristics of pulses within a PPG signal may be used, for example, in blood pressure measurements, and therefore, the quality of the measurement may depend on the shape of the PPG signal pulses. By using a metric to quantify the shape of a PPG derivative signal, or any physiological signal, measurement quality can be monitored and used to improve the operation of patient monitoring devices.

One such metric is the skewness of the signal, which generally refers to the asymmetry of a signal around its mean or average value. Such a metric captures, for example, the initial high-magnitude negative portion and subsequent low-magnitude positive portion of a pulse of the PPG time derivative signal. Other skewness metrics that capture this shape may include the ratio of the positive area or peak of the PPG time derivative signal to the negative area or peak of the PPG time derivative signal, or the ratio of the duration of the upstroke to the duration of the downstroke of the PPG signal.

A skewness measure of a signal may be used to identify short- or long-term changes in the morphology of the signal. For example, the skewness of a PPG time derivative signal may be compared to that measured at a calibration point or a previously recorded characteristic skewness (for example the mean or median skewness during a prior time period). A transient, or short-term, change in skewness may indicate a region of noise in the signal where the measurements should be ignored or treated appropriately in a filtering operation (e.g., given a lower weighting in an average). A long-term change in skewness may indicate a change in signal morphology, which in turn may indicate a change in, for example, patient posture or blood vessel compliance.

Additionally, a skewness measure may be advantageously employed in continuous, non-invasive blood pressure (CNIBP) monitoring systems that estimate blood pressure based at least in part on a differential pulse transit time (DPTT) determination. The DPTT, which measures the difference in arrival times of a cardiac pulse between two body sites, may be used through a known relationship of the change in DPTT with blood pressure to determine the instantaneous blood pressure of a patient subsequent to a calibration measure from a calibration device. Measuring DPTT may be based at least in part on the use of two sensors, each placed at one of the two body sites. Comparing skewness measures between the signals received at each of the two sensors may, for example, reveal when noise is adversely affecting one channel, or when, for example, a patient has undergone a change in condition which manifests in different signal shape changes at the two channels.

Deriving and analyzing shape metrics, including skewness metrics, from physiological signals in the manner described herein allows determinations of measurement quality, physiological changes, and monitoring system operating conditions to be made. Such determinations may be used for any number of functions, including indicating to a patient or care provider that the measurement quality is low or unacceptable, alerting a patient or care provider to a change in patient status, triggering or delaying a recalibration of a monitoring device, adjusting the operating parameters of a monitoring system, any other suitable function, or any combination thereof.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1A:
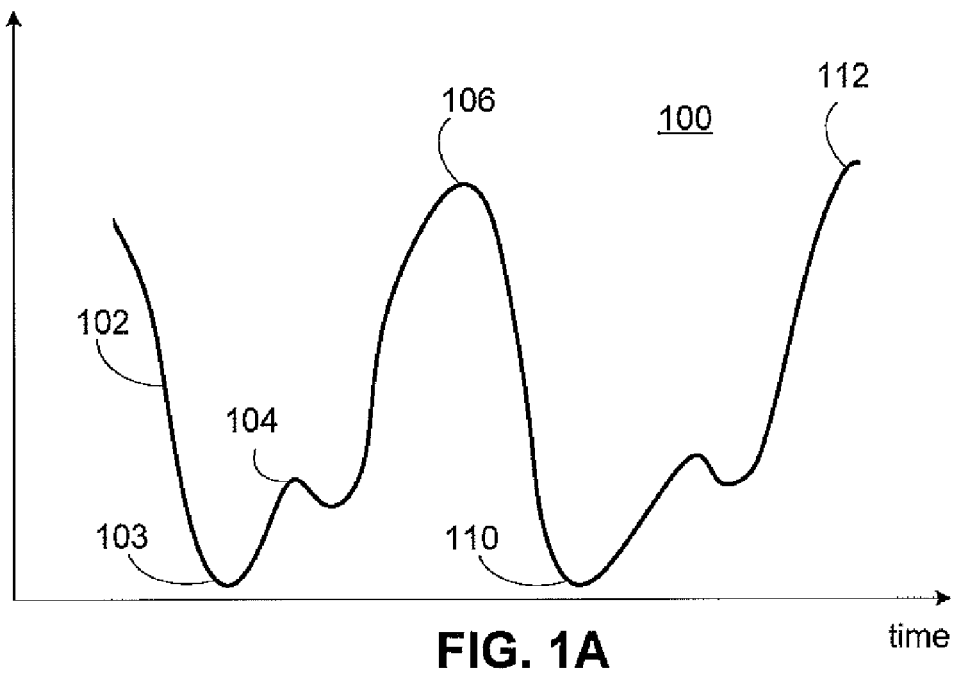
FIGS. 1A-1B depict an illustrative photoplethysmograph (PPG) signal and its time derivative signal, respectively, in accordance with an embodiment.

Electronic patient monitors play a critical role in medical diagnosis and treatment, both inside and outside the clinical setting. Such monitors are often able to detect changes in a patient's physiological function that may indicate a dangerous condition before noticeable symptoms occur. In particular, monitors that analyze a patient's physiological signals can often perform calculations that uncover dangerous conditions that are difficult for a human clinician to detect from displayed signals alone.

There are many factors that determine the efficacy of a patient monitoring system. One of these factors is the quality of the physiological measurement or measurements at the monitoring device from the patient. A high quality measurement is one that communicates useful information about the underlying physiological process of interest. The quality of the measurement resulting from a received electronic signal can be degraded by, for example, electromagnetic coupling from other electronic instruments, movement of the patient, and environmental factors that interfere with the connection between the patient and the monitoring device.

Another factor that contributes to the efficacy of a patient monitoring system is the accuracy of the relationship between the electronic signal received at a monitoring device and the physiological process itself. This relationship is often referred to as the "calibration" and may be stored within the monitoring device. In an embodiment, the patient monitoring system is a CNIBP system that provides blood pressure readings based at least in part on measurements of a differential pulse transit time (DPTT), which is the difference in the arrival times of a cardiac pulse at two or more body sites. Such monitoring systems may include two or more sensors, each located at one of the two or more body sites, respectively. However, this stored relationship may not always be accurate, decreasing the usefulness of the monitoring system. Monitoring devices are often recalibrated by comparison with a calibration device that serves as a known reference. For example, calibrating a CNIBP system may include making two DPTT measurements and comparing the change in DPTT against calibration measures from a calibration device using a known relationship between the change in DPTT and blood pressure. Recalibrations may be performed according to a fixed schedule. In one suitable approach, a monitoring device may be recalibrated when the monitored physiological process undergoes a change (e.g., when a patient changes position).

While the present disclosure is predominantly described in the context of a CNIBP monitoring system, it will be understood that the present disclosure may be applied to any other suitable physiological monitoring systems, such as pulse oximetry systems, ECG systems, any other suitable system, or any combination thereof.

Changes in the shape of a physiological signal waveform may communicate information about both measurement quality and the need for recalibration. For example, changes in the shape of a waveform may suggest the introduction of a new noise source into the monitoring environment, indicating decreased measurement quality. Such a change may also suggest that recalibration be delayed until an improvement in measurement quality is detected. Changes in the shape of a waveform may also result when, for example, a patient is given a drug which alters their physiological state, requiring a recalibration of the monitoring device. Accordingly, there is a need for monitoring devices that employ computationally-efficient metrics for determining changes in shape of signal waveforms and that use this information to perform monitoring operations. The methods and systems described herein address these needs by determining skewness values of physiological signals and using these skewness values to initiate the recalibration of the device. Additionally, the techniques described herein provide methods and systems that adjust monitoring and recalibration parameters based at least in part on shape-based measurement quality metrics.

Figure 1B:
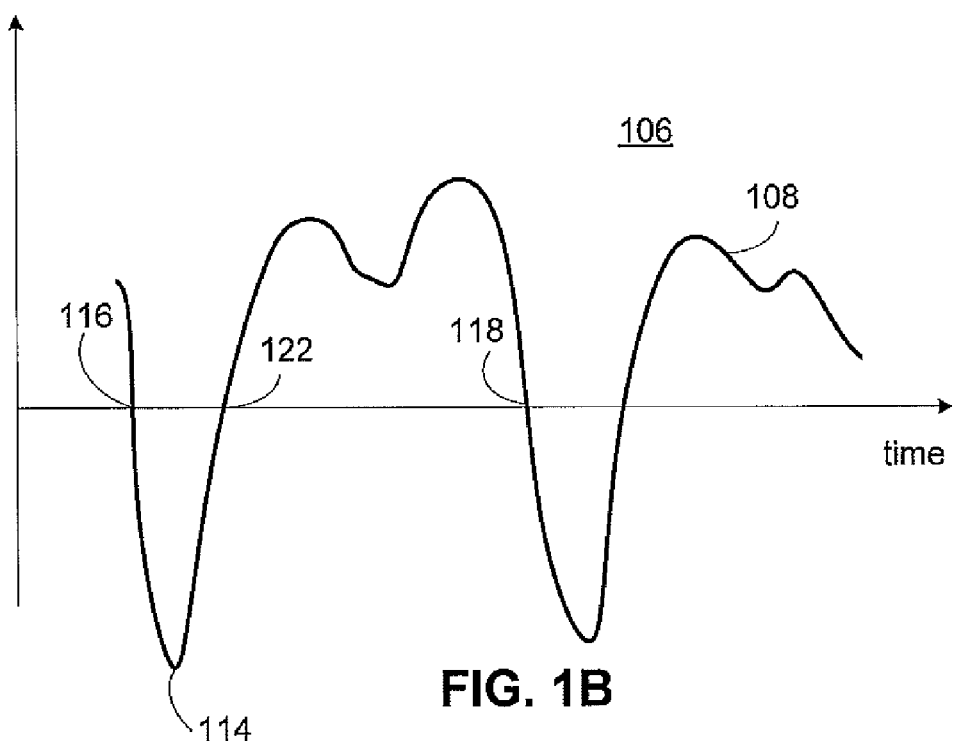

The methods and systems of the present disclosure will be illustrated with reference to the monitoring of a photoplethysmograph (PPG) signal; however, it will be understood that the disclosure is not limited to monitoring PPG signals and is usefully applied within a number of patient monitoring settings. FIGS. 1A-1B depict an illustrative photoplethysmograph (PPG) signal 102 and its time derivative signal 108, respectively. Such signals may arise from, for example, an oximetry system. An oximetry system may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. The oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the PPG signal. In addition, the term "PPG signal," as used herein, may also refer to an absorption signal (i.e., representing the amount of light absorbed by the tissue) or any suitable mathematical manipulation thereof. The time derivative of the PPG signal may also be of interest, and the term "PPG time derivative signal" will be used herein. In an embodiment, the PPG signal and/or the PPG time derivative signal may be used to calculate the amount of the blood constituent (e.g., oxyhemoglobin) being measured as well as the pulse rate and when each individual pulse occurs.

A high quality PPG signal may be characterized by a sharp initial downstroke, corresponding to the beginning of a single pulse wave (e.g., the portion of PPG signal 102 between point 106 and point 110 in the plot 100 of FIG. 1A). Typical PPG signals from a healthy patient may go up and down once per pulse, or may have a small dicrotic notch (e.g., notch 104) on the upstroke, on the downstroke, in the middle, or adjacent to the pulse. The initial downstroke may drop quickly to a trough, then may rise to a maximum value on an upstroke that extends over a longer period of time (e.g., the portion of PPG signal 102 between point 110 and point 112). Consequently, the time derivative of such a waveform may include an initial portion with a highly negative initial amplitude, corresponding to the steep downstroke (e.g., in plot 106 of FIG. 1B, the portion of PPG time derivative signal 108 between point 116 and point 122, with highly negative initial peak 114), followed by a second portion with a positive amplitude of lower amplitude, corresponding to the gradual upstroke (e.g., the portion of PPG time derivative signal 108 between point 122 and point 118). Such signals are often well-characterized by a skewness metric. Skewness metrics generally measure the asymmetry of a signal around a mean or average value. Skewness metrics may be advantageously applied to PPG signals and PPG time derivative signals to characterize the degree of asymmetry and hence the shape of such signals.

Figure 2:
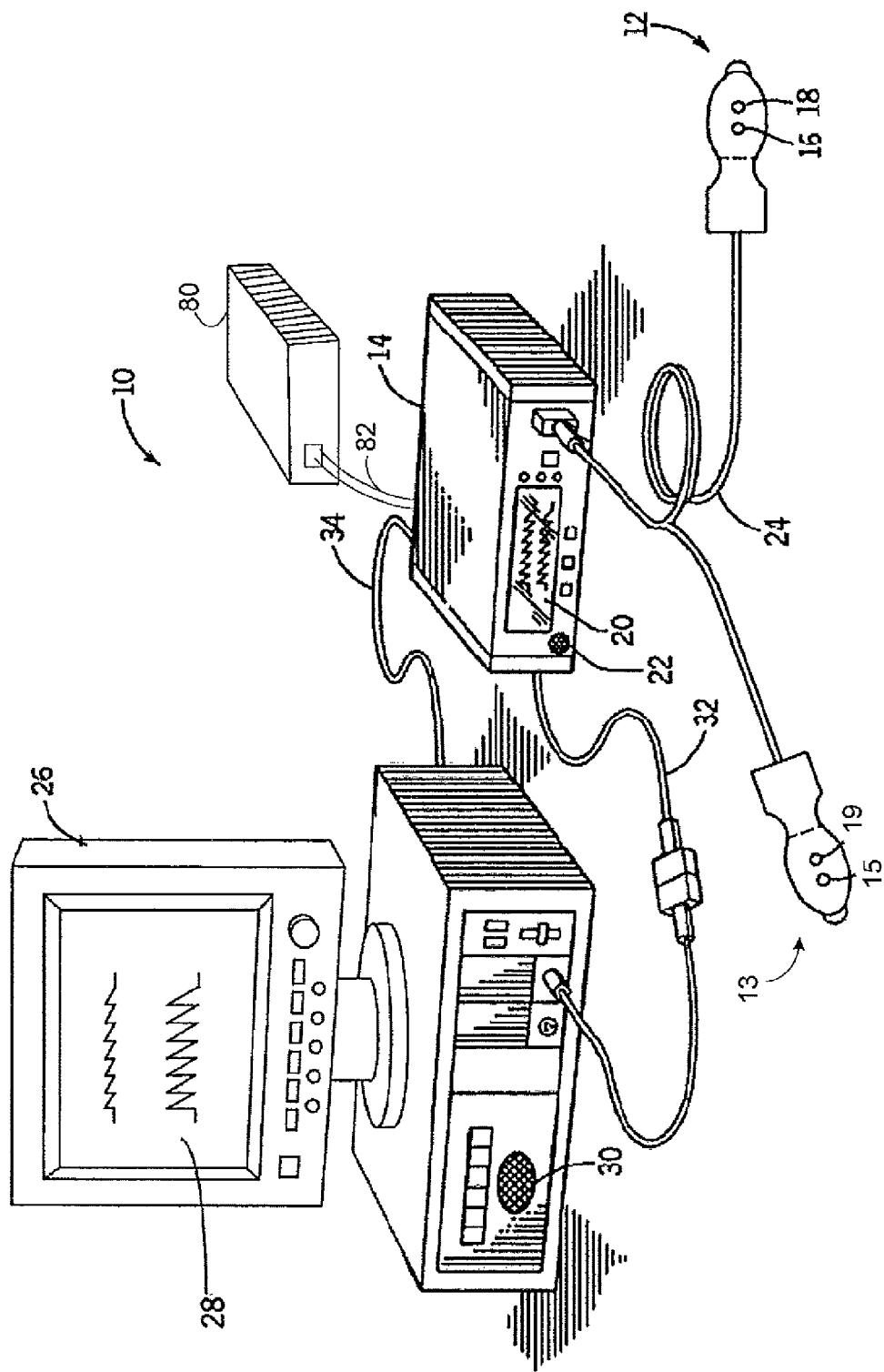
FIG. 2 shows an illustrative patient monitoring system in accordance with an embodiment.

FIG. 2 shows an illustrative patient monitoring system 10. System 10 may include a sensor unit 12 and a monitor 14. In an embodiment, sensor unit 12 is part of a continuous, non-invasive blood pressure (CNIBP) monitoring system and includes sensors 16 and 18 positioned at two different locations on a subjects body. Although sensors 16 and 18 are depicted as being in close proximity within sensor unit 12, sensors 16 and 18 may be capable of positioning on a patient's body at locations spaced apart. For example, sensor 16 may be positioned on a patient's forehead, while sensor 18 may be positioned at a patient's fingertip. Any suitable physical configuration of sensors 16 and 18 may be used. In an embodiment, system 10 may include one or more additional sensor units, such as sensor unit 13, which may take the form of any of the embodiments described herein with reference to sensor unit 12. For example, sensor unit 13 may include two sensors 15 and 19. Sensor unit 13 may be the same type of sensor unit as sensor unit 12, or sensor unit 13 may be of a different sensor unit type than sensor unit 12. As discussed in additional detail below, one or more signals from one or more sensors and/or sensor units may be used in the measurement assessment techniques described herein.

In some embodiments, the signal obtained from the single sensor or probe may take the form of a PPG signal obtained, for example, from a CNIBP monitoring system or pulse oximeter. Sensors 16 and 18 may each detect any signal that carries information about a patient's physiological state, such as an electrocardiograph signal, arterial line measurements, or the pulsatile force exerted on the walls of an artery using, for example, oscillometric methods with a piezoelectric transducer. According to another embodiment, system 10 may include a plurality of sensors forming a sensor array in lieu of either or both of sensors 16 and 18. Although only two sensors 16 and 18 are illustrated in the sensor unit 12 of FIG. 3, it is understood that any number of sensors measuring any number of physiological signals may be used to assess patient status in accordance with the techniques described herein.

In an embodiment, sensors 16 and 18 are combined within a single sensor capable of detecting a single signal. In an embodiment, this sensor may be a pulse oximeter. In this embodiment, sensor unit 12 may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. The light intensity or the amount of light absorbed may then be used to calculate physiological measurements, including blood pressure (BP). Techniques for obtaining BP measurements from oximetry data are described in more detail in co-pending, commonly assigned U.S. patent application Ser. No. 12/242,867, filed Sep. 30, 2008, entitled "SYSTEMS AND METHODS FOR NON-INVASIVE CONTINUOUS BLOOD PRESSURE DETERMINATION" and co-pending, commonly assigned U.S. patent application Ser. No. 12/242,238, filed Sep. 30, 2008, entitled "LASER SELF-MIXING SENSORS FOR BIOLOGICAL SENSING," which are both hereby incorporated by reference herein in their entireties.

In an embodiment, sensor unit 12 may include a laser Doppler sensor. Techniques for obtaining information about blood pressure from self-mixed laser Doppler sensors are described in more detail in co-pending, commonly assigned U.S. patent application Ser. No. 12/242,738, filed Sep. 30, 2008, entitled "LASER SELF-MIXING SENSORS FOR BIOLOGICAL SENSING," which is incorporated by reference herein in its entirety.

It will be understood that the present disclosure is applicable to any suitable signals that communicate information about an underlying physiological process. It will be understood that the signals may be digital or analog. Moreover, it will be understood that the present disclosure has wide applicability to signals including, but not limited to other biosignals (e.g., electrocardiogram, electroencephalogram, electrogastrogram, phonocardiogram, electromyogram, pathological sounds, ultrasound, or any other suitable biosignal), or any combination thereof. For example, the techniques of the present disclosure could be applied to monitoring pathological sounds or arterial (or venous) pressure fluctuations.

In an embodiment, sensor unit 12 may be connected to and draw its power from monitor 14 as shown. In another embodiment, sensor unit 12 may be wirelessly connected to monitor 14 and include its own battery or similar power supply (not shown). In an embodiment, sensor unit 12 may be communicatively coupled to monitor 14 via a cable 24. However, in other embodiments, a wireless transmission device (not shown) or the like may be used instead of or in addition to cable 24.

Monitor 14 may be configured to calculate physiological parameters (e.g., heart rate and blood pressure) based at least in part on data received from sensor unit 12. In an alternative embodiment, the calculations may be performed on the monitoring device itself and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments to be discussed further below, such as for example, sounding an audible alarm in the event that a patient's physiological parameters are not within a predefined normal range. Monitor 14 may also include a measurement quality indicator, such as a graphic or text in display 20 or a tone or message via speaker 22.

In the illustrated embodiment, system 10 may also include a multi-parameter patient monitor 26. The monitor 26 may include a cathode ray tube display, a flat panel display (as shown) such as a liquid crystal display (LCD) or a plasma display, or may be any other type of monitor. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "$SpO_2$" measurement), and pulse rate information from monitor 14. Monitor 26 may include a speaker 30, and may include a measurement quality indicator as discussed above with reference to monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14 via a cable 82, a battery, or by a conventional power source such as a wall outlet, may include any suitable physiological signal calibration device. Calibration device 80 may be communicatively coupled to monitor 14 via cable 82, and/or may communicate wirelessly (not shown). For example, calibration device 80 may take the form of any invasive or non-invasive physiological monitoring or measuring system used to generate reference physiological measurements for use in calibrating a monitoring device. For example, calibration device 80 may take the form of a blood pressure monitoring system, and may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference physiological measurements obtained from some other source (e.g., an external invasive or non-invasive physiological measurement system).

Calibration device 80 may also access reference measurements stored in memory (e.g., RAM, ROM, or a storage device). As described in more detail below, the reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference blood pressure measurements may then be wirelessly transmitted to monitor 14 for use in calibration. In still other embodiments, calibration device 80 is completely integrated within monitor 14. For example, in some embodiments, calibration device 80 may access reference measurements from a relational database stored within calibration device 80, monitor 14, or multiparameter patient monitor 26. As described in additional detail below, calibration device 80 may be responsive to an electronic recalibration signal, which may initiate the calibration of monitor 14 or may communicate recalibration information to calibration device 80 (e.g., a recalibration schedule). Calibration may be performed at any suitable time (e.g., once initially after monitoring begins) or on any suitable schedule (e.g., a periodic or event-driven schedule). In an embodiment, calibration may be initiated or delayed based at least in part on a measurement quality assessment or a recalibration initiation assessment of an electronic signal representing a physiological process.

Figure 3:
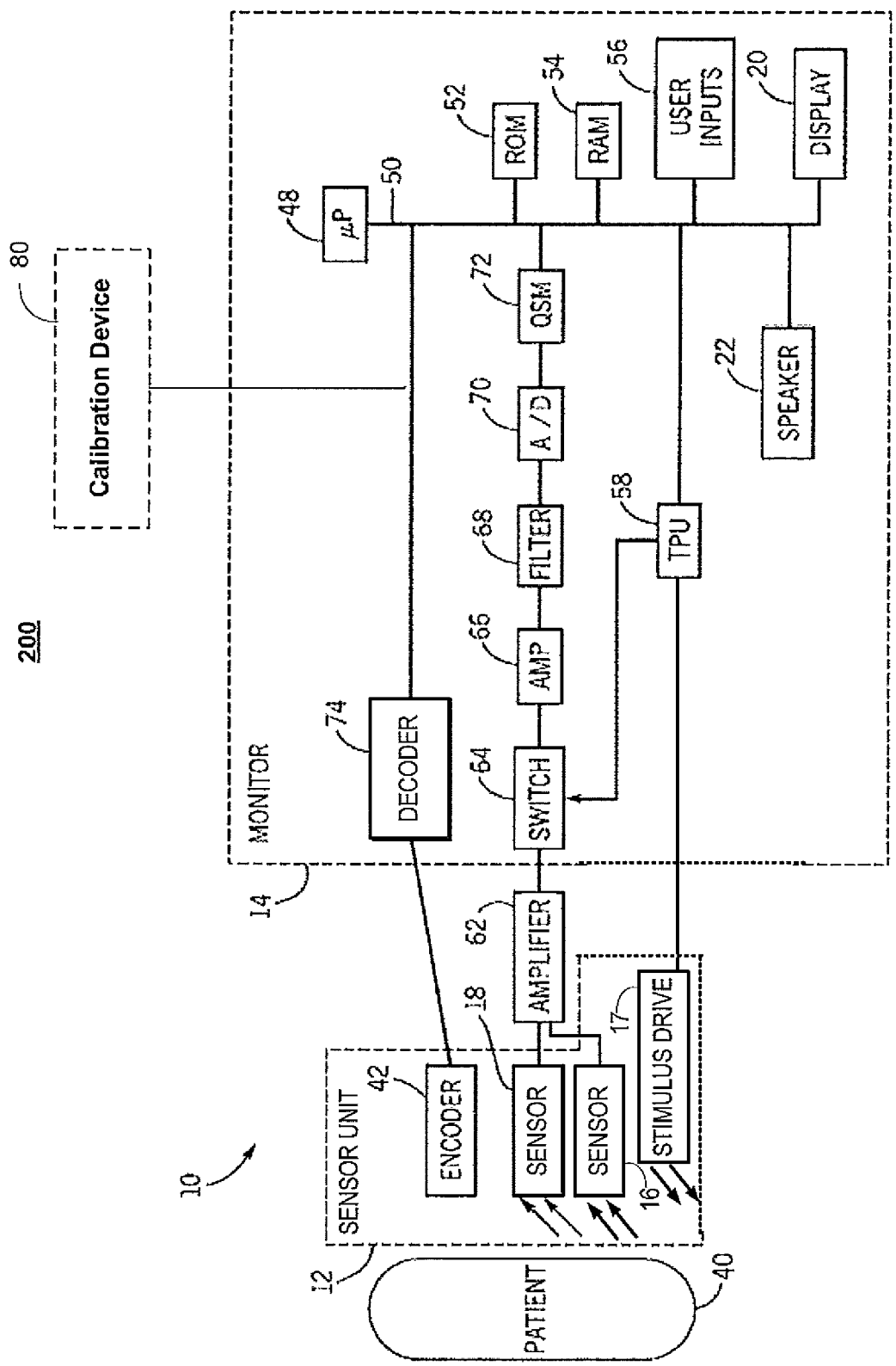
FIG. 3 is a block diagram of an illustrative patient monitoring system coupled to a patient in accordance with an embodiment.

FIG. 3 is a block diagram of a patient monitoring system 200, such as system 10 of FIG. 2, which may be coupled to a patient 40 in accordance with an embodiment. Certain illustrative components of sensor unit 12 and monitor 14 are illustrated in FIG. 3.

Sensor unit 12 may include encoder 42. In an embodiment, encoder 42 may contain information about sensor unit 12, such as what type of sensors it includes (e.g., whether the sensor is a pressure transducer or a pulse oximeter). This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information about a patient's characteristics may allow monitor 14 to determine, for example, patient-specific threshold ranges in which the patient's physiological parameter measurements should fall and to enable or disable additional physiological parameter algorithms. This information may also be used to select and provide coefficients for equations from which BP and other measurements may be determined based at least in part on the signal or signals received at sensor unit 12. For example, some pulse oximetry sensors rely on equations to relate an area under a pulse of a photoplethysmograph (PPG) signal to determine BP. These equations may contain coefficients that depend upon a patient's physiological characteristics as stored in encoder 42. In some embodiments, encoder 42 may include a memory or a coded resistor which stores one or more of the following types of information for communication to monitor 14: the types of sensors included in sensor unit 12; the wavelength or wavelengths of light used by an oximetry sensor when included in sensor unit 12; a signal threshold for each sensor in the sensor array; any other suitable information; or any combination thereof. Encoder 42 may also include information about the recalibration requirements of the sensors included in sensor unit 12, including any one of a nominal frequency of recalibration and preferred recalibration conditions.

In an embodiment, signals from sensor unit 12 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a stimulus drive 17, which may control when a stimulus is used to apply a signal to the patient, the response to which communicates information about the patient's physiological processes. For example, stimulus drive 17 may be a light emitter in an oximetry configuration. Techniques for obtaining physiological measurements by inducing perturbations in a patient via a stimulus drive are described in more detail in co-pending, commonly assigned U.S. patent application Ser. No. 12/248,738, filed Oct. 9, 2008, entitled "SYSTEMS AND METHODS USING INDUCED PERTURBATION TO DETERMINE PHYSIOLOGICAL PARAMETERS," which is incorporated by reference herein in its entirety. TPU 58 may also control the gating-in of signals from sensor unit 12 through an amplifier 62 and a switching circuit 64. The received signal or signals from sensor unit 12 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple sensors included in sensor unit 12.

In an embodiment, microprocessor 48 may determine the patient's physiological parameters, such as BP, using various algorithms and/or look-up tables based at least in part on the value of the received signals and/or data from sensor unit 12. For example, when sensor unit 12 includes an oximetry sensor, microprocessor 48 may generate an equation that represents empirical data associated with one or more patients that includes various BP measurements associated with different areas under a pulse of a PPG signal. Signals corresponding to information about patient 40 may be transmitted from encoder 42 to a decoder 74. These signals may include, for example, encoded information relating to patient characteristics. Decoder 74 may translate these signals to enable the microprocessor to determine the thresholds based at least in part on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

Patient monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described above, reference measurements from calibration device 80 may be accessed by microprocessor 48 for use in calibrating the sensor measurements and determining physiological signals from the sensor signal and empirical data of one or more patients.

As discussed above, the signal from the patient can be degraded by noise, among other sources. One source of noise is electromagnetic coupling from other electronic instruments. Movement of the patient also introduces noise and affects the signal. For example, the contact between the sensor and the skin can be temporarily disrupted when movement causes either to move away from the skin. Another source of noise is ambient light that reaches the light detector in an oximetry system.

Noise (e.g., from patient movement) can degrade a sensor signal relied upon by a care provider, without the care provider's awareness. This is especially true if the monitoring of the patient is remote, the motion is too small to be observed, or the care provider is watching the instrument or other parts of the patient, and not the sensor site. Processing sensor signals may involve operations that reduce the amount of noise present in the signals or otherwise identify noise components in order to prevent them from affecting measurements of physiological parameters derived from the sensor signals.

Figure 4:
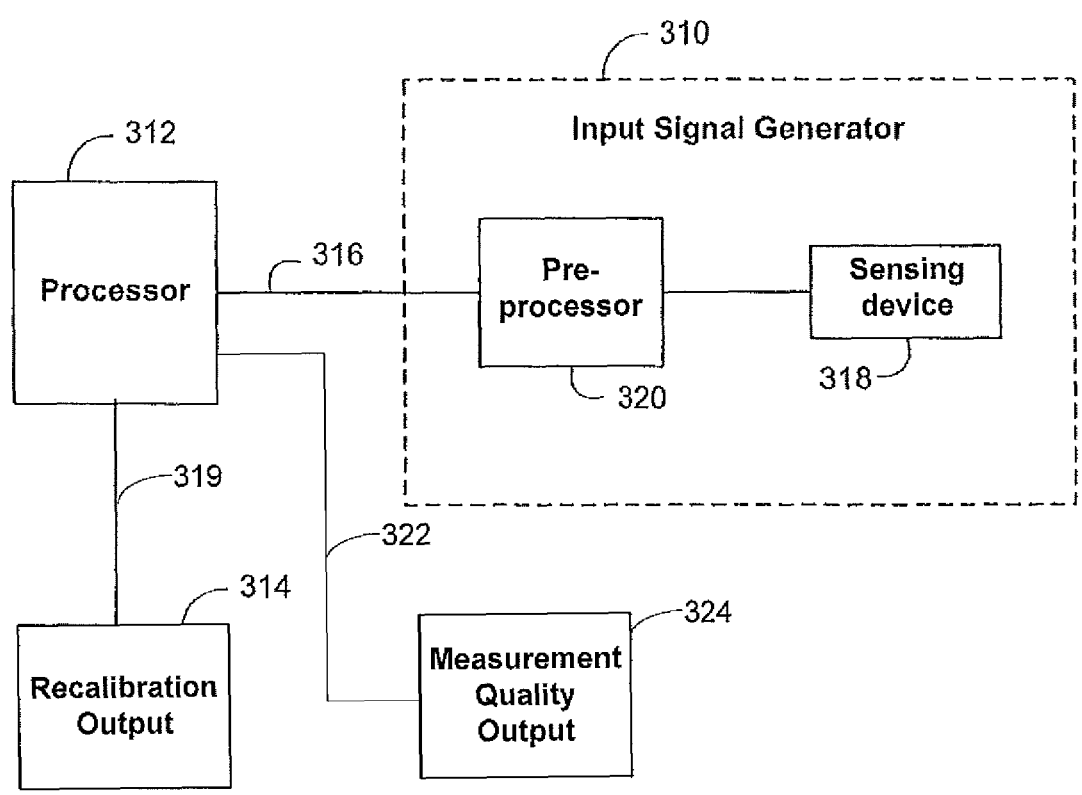
FIG. 4 is a block diagram of an illustrative signal processing system in accordance with an embodiment.

FIG. 4 is an illustrative processing system 300 in accordance with an embodiment. In an embodiment, input signal generator 310 generates an input signal 316. As illustrated, input signal generator 310 includes pre-processor 320 coupled to sensing device 318. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing techniques to the signal generated by sensing device 318. For example, pre-processor 320 may apply a predetermined transformation to the signal provided by the sensing device 318 to produce an input signal 316 that can be appropriately interpreted by processor 312. Pre-processor 320 may also perform any of the following operations to the signal provided by the sensing device 318: reshaping the signal for transmission; multiplexing the signal; modulating the signal onto carrier signals; compressing the signal; encoding the signal; and filtering the signal.

In the embodiment of FIG. 4, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may, for example, be configured of analog electronic components. Processor 312 may perform some or all of the calculations associated with the recalibration initiation and measurement quality monitoring methods of the present disclosure. For example, processor 312 may compute a skewness value of a received signal and compare this skewness value to a threshold. Processor 312 may also generate a suitable recalibration signal, a suitable measurement quality signal, or both, and transmit these signals to calibration device 80 and display 20, respectively. Processor 312 may also perform any suitable signal processing to filter signal 316, such as any suitable band-pass filtering, adaptive filtering, closed-loop filtering, and/or any other suitable filtering, and/or any combination thereof. Processor 312 may also receive input signals from additional sources (not shown). For example, processor 312 may receive an input signal containing information about treatments provided to the patient. These additional input signals may be used by processor 312 in any of the calculations or operations it performs in accordance with the patient monitoring system 300.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In an embodiment, processor 312 may store physiological measurements or previously received data from signal 316 in a memory device for later retrieval. In an embodiment, processor 312 may store calculated values, such as skewness values, in a memory device for later retrieval.

Processor 312 may determine the locations of pulses within the signal 316. For example, processor 312 may identify within the PPG signal of FIG. 1A, local minimum point 103, local maximum point 106, local minimum point 110, and local maximum point 112 in the PPG signal Processor 312 may pair points to define segments. Processor 312 may pair each local minimum point with a following, adjacent maximum point. For example, processor 312 430 may pair points 103 and 106 to identify one segment and points 110 and 112 to identify a second segment. The location and slope of a segment may be measured to determine what portion of the pulse the segment corresponds to, for example an upstroke (e.g., a positive slope) or downstroke (e.g., a negative slope) portion of the pulse. The pulse is defined as a combination of at least one upstroke and one downstroke. For example, the segment identified by points 103 and 106 and the segment identified by points 106 and 110 may define a pulse.

Processor 312 may also identify additional characteristic points within the signal 316. According to an embodiment, PPG signal 102 may include a dicrotic notch 104 or other notches (not shown) in different sections of the pulse. For example, a notch may occur, at the beginning of a pulse (referred to as an ankle notch), in the middle of a pulse (referred to as a dicrotic notch), or near the top of a pulse (referred to as a shoulder notch). Pulse detection techniques performed by processor 312 are described in more detail in co-pending, commonly assigned U.S. patent application Ser. No. 12,242,908, filed Sep. 30, 2008, entitled "SYSTEMS AND METHODS FOR DETECTING PULSES," which is incorporated by reference herein in its entirety.

In an embodiment, processor 312 derives and analyzes a shape metric from signal 316 to detect changes in the shape of the waveform. In an embodiment, processor 312 may identify individual pulses using any of the techniques described herein, then derive and analyze the shape metric from each individual pulse. The shape metric may be a skewness metric. A skewness metric generally measures the asymmetry of a signal around its mean or average value. Such embodiments are discussed in additional detail below with reference to FIGS. 5-7.

Processor 312 may be coupled to a calibration device 80 that may generate or receive as input reference measurements for use in calibrating calculations. This coupling may occur through recalibration signal 319 and recalibration output 314, and may occur through additional signal pathways not shown. In an embodiment, recalibration output 314 is connected to or in communication with calibration device 80 and is capable of transmitting a command to calibration device 80 to a recalibration procedure. Recalibration output 314 may simply pass recalibration signal 319 to calibration device 80, or may transform the information in recalibration signal 319 into a form suitable for calibration device 80.

Processor 312 may be coupled to measurement quality output 324, between which measurement quality signal 322 may be communicated. Measurement quality output 324 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof, one or more printing devices, any other suitable output device, or any combination thereof. In an embodiment, measurement quality signal 322 may include any one or more of a measurement quality value representative of current measurements, past measurements, identification of a noise source, a low measurement quality alert, and a current physiological measurement. In some embodiments, measurement quality signal 322 may be stored in a memory device or recorded in another physical form for future, further analysis.

In an embodiment, measurement quality signal 322 may be transmitted to recalibration output 314. Recalibration output 314 may then transmit a command to calibration device 80 based at least in part on measurement quality signal 322. In an embodiment, recalibration signal 319 may be is generated by the processor 312 based at least in part on a measurement quality value, the measurement quality signal 322, or both.

It will be understood that system 300 may be incorporated into system 10 (FIGS. 2 and 3) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch, other piece of jewelry, or cellular telephone). In such embodiments, a wireless transceiver (not shown) may also be included in system 300 to enable wireless communication with other components of system 10. As such, system 10 may be part of a fully portable and continuous patient monitoring solution.

Figure 5:
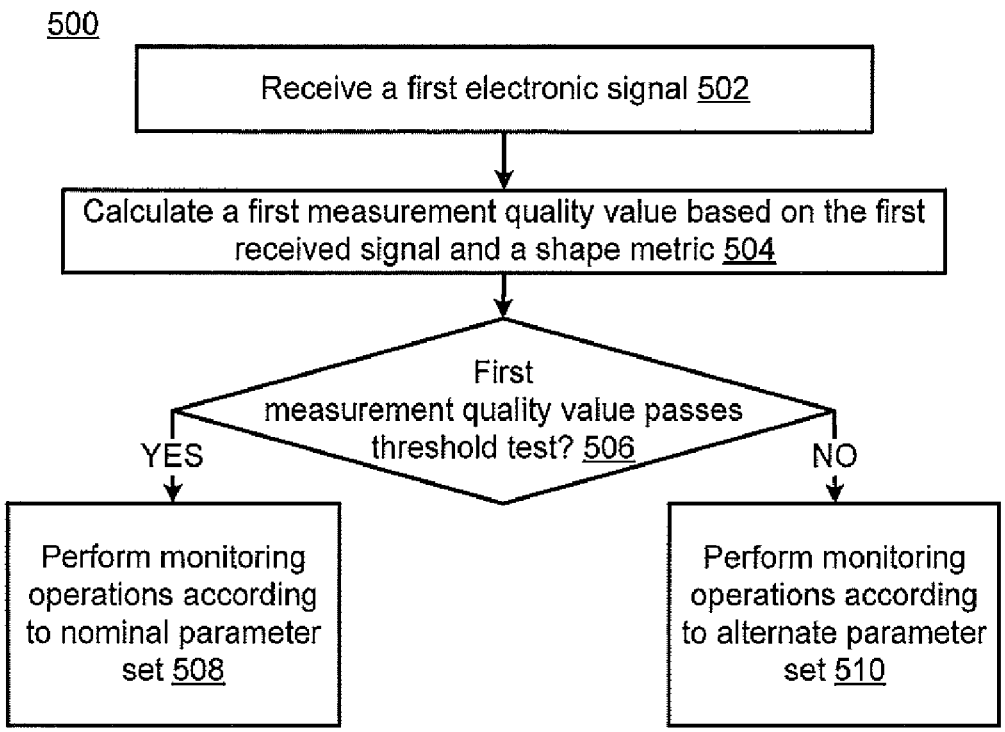
FIG. 5 is a flow diagram of illustrative steps involved in patient monitoring utilizing a measurement quality assessment in accordance with an embodiment.

FIG. 5 is a flow diagram of illustrative steps involved in patient monitoring utilizing a measurement quality assessment in accordance with an embodiment. Process 500 may be performed by processor 312, or may be performed by any suitable processing device communicatively coupled to monitor 14. At step 502, a first electronic signal is received. This first electronic signal may be representative of a physiological process, and may be generated by sensor unit 12, which may itself include any of the number of physiological sensors described herein. The received first signal may be signal 316, which may be generated by a pre-processor 320 coupled between processor 312 and sensing device 318. The received first signal may include multiple signals, for example, in the form of a multi-dimensional vector signal or a frequency- or time-multiplexed signal. Additionally, the first electronic signal received in step 502 may be a derived signal generated internally to processor 312. Accordingly, the first received signal may be a transformation of a signal 316, or may be a transformation of multiple such signals. For example, the first electronic signal may be a ratio of two signals. The first received signal may be based at least in part on past values of a signal, such as signal 316, which may be retrieved by processor 312 from a memory such as a buffer memory or RAM 54.

Once a first electronic signal is received at step 502, a first measurement quality value of the received first signal may be calculated based at least in part on a shape metric at step 504. In an embodiment, a shape metric may be applied to a single pulse or multiple pulses. In an embodiment, a shape metric may be applied to a portion of the first electronic signal within a time window. Generally, "time window" may be used to refer to either an interval of time, a number of pulses, or a combination of the two. The time window over which the shape metric is applied may include past values of the first electronic signal. The shape metric may be any quantification of the shape or change in shape of the first electronic signal or a transformation of the first electronic signal. In an embodiment, the shape metric is applied to the first electronic signal over a first time window and a second time window, then the values of the shape metric over each window are combined (e.g., by taking a difference, an absolute difference, or a ratio). Examples of such shape metrics include:

1. The peak amplitude of a previous pulse.
2. The period of a previous pulse.
3. The path length of a previous pulse, defined as the sum of the absolute values of the differences between subsequent samples taken over the duration of the pulse.
4. For signals that include two or more components (e.g., associated with each of the red and infrared frequency ranges in an PPG monitoring system), a ratio of a characteristic of each of the components (e.g., an amplitude or period).
5. The ratio of a duration of the downstroke and a duration of the upstroke from one or more signals and/or one or more pulses.

Shape metrics may also include normalized and generalized versions of metrics described herein, and may be applied to one or more pulses or time windows and combined via any suitable transformation. For example, the first measurement quality value may be based at least in part on a change of shape between two instances or windows of the received first signal. The shape metric may be a skewness metric, as discussed in additional detail below.

In an embodiment, the patient monitoring system is a CNIBP system that provides blood pressure readings based at least in part on measurements of a differential pulse transit time (DPTT). Such monitoring systems may include two or more sensors and the skewness of the signals transmitted by of the two sensors may be compared and tracked over time to detect the need for recalibration, for example, by comparing skewness ratios calculated at times T1 and T2, as described above with reference to process 500. For example, if noise is introduced into the signal transmitted by only the first sensor, or if the first sensor malfunctions or is dislodged, the shape of the waveform transmitted by the first sensor will be different from time T1 to time T2 and this difference will be reflected in different first and second ratios.

At step 506, the first measurement quality value is subject to a threshold test. Generally, a threshold test on a value may test any of a number of threshold conditions, including whether the value exceeds a single threshold, whether the value is below a single threshold, or whether the value falls within a specified range or ranges. The threshold test may be fixed, and retrieved by processor 312 from ROM 52 or RAM 54. The threshold test may be dynamic and depend, for example, on past values of the received first signal, the first measurement quality value, or both. In an embodiment, the threshold test may compare the measurement quality value to the value of a shape metric applied to a past time window of the first electronic signal. In an embodiment, the threshold test may depend on values of the shape metric applied to multiple time windows. For example, a single threshold may be the average of the shape metric applied to a fixed number of past time windows, or may be this average minus a multiple of standard deviations of the shape metric values. When the measurement quality value exceeds this single threshold, the threshold test is passed. The threshold test may also depend on secondary signal quality indicators, such as an electromagnetic noise measuring device or a signal arising from sensor device 318 indicating a malfunction or undesirable operating condition. In the DPTT measurement example described above, the absolute difference between the first and second ratios may be compared against a threshold to determine whether a significant change in measurement quality has occurred.

If it is determined at step 506 that the first measurement quality value passes the threshold test, the process 500 may proceed to step 508 and monitoring operations may be performed according to a nominal set of parameters. This nominal parameter set may correspond to a "normal" operating state of the patient monitoring system. Such a set of parameters may include displaying a measurement calculated from the first electronic signal on at least one of display 20 and display 28, storing the calculated measurement (e.g., in RAM 54), using the calculated measurement in other calculations performed by the system, or any combination thereof. Such calculations may include a patient condition estimation routine or a patient status prediction routine.

If it is determined at step 506 that the first measurement quality value does not pass the threshold test, the process 500 may proceed to step 510 and the system may perform monitoring operations according to an alternate set of parameters. This alternate parameter set may correspond to a "low measurement quality" operating state of the patient monitoring system. Such a state may indicate reduced confidence in the ability of the first electronic signal to communicate information about a physiological process. The corresponding parameter set may include displaying a "low quality" warning signal via display 20 or display 28, or an audible warning via speaker 22 or speaker 30. The parameter set may also include suppressing the display of a measurement calculated from the first electronic signal, suppressing the storing of the calculated measurement, suppressing the use of the calculated measurement in other calculations performed by the system, or any combination thereof.

In an embodiment, steps 506, 508 and 510 need not be performed. Instead, the patient monitoring system may use the first measurement quality signal to adjust monitoring operations that may be based at least in part on the first electronic signal. For example, multi-parameter monitor 26 may provide a measurement estimate of a physiological process on display 28. This measurement estimate may be calculated by processor 312 as a running average of measurements made based at least in part on the received first signal over a time window. The first measurement quality value calculated in step 504 may be used to determine the length of this time window, with lower quality values suggesting wider time windows and vice versa. Alternately, the length of the time window may be fixed, but each measurement within the window may be weighted within the running average by its associated measurement quality value. In such an embodiment, a low quality measurement may have relatively less influence on the measurement estimate displayed by multi-parameter monitor 26 than under a "nominal" parameter set.

Figure 6:
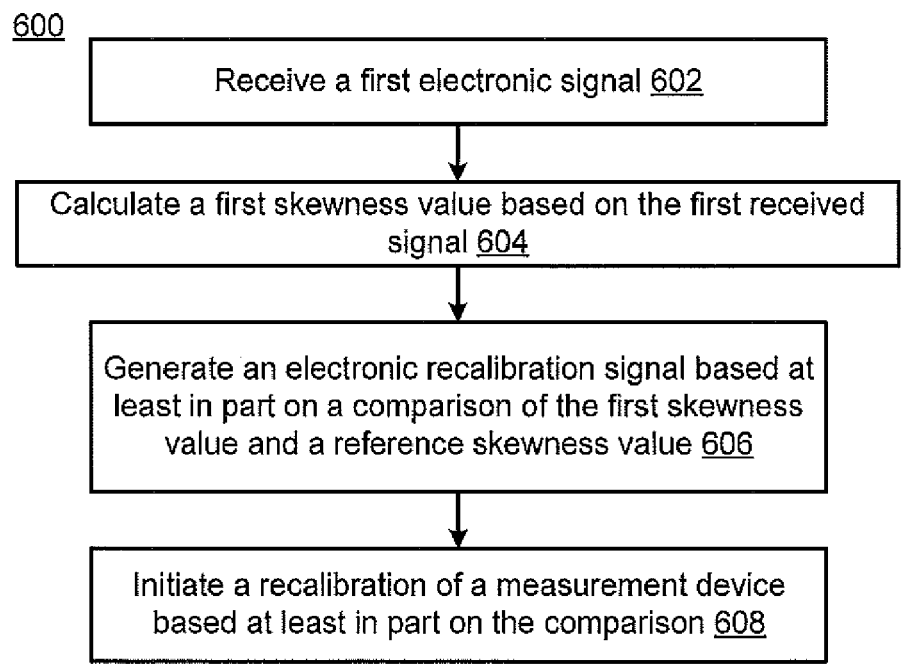
FIGS. 6-7 are flow diagrams of illustrative steps involved in recalibration initiation processes, each in accordance with an embodiment.

FIG. 6 is a flow diagram of an illustrative recalibration initiation process 600 in accordance with an embodiment. Process 600 may be performed by processor 312, or may be performed by any suitable processing device communicatively coupled to monitor 14. At step 602, a first electronic signal is received. Embodiments of step 602 may include, for example, any of the embodiments described above with reference to step 502 of process 500.

Once a first electronic signal is received at step 602, a first skewness value may be calculated based at least in part on the received first signal at step 604. In an embodiment, the first skewness value includes deriving and analyzing a skewness metric from a time window of the received first signal, the time derivative of the received first signal, or any transformation of the received first signal. In an embodiment, a skewness value of a signal may be calculated as any of the following illustrative skewness metrics:

1. A sample skewness in accordance with $$\frac{\frac{1}{n}\sum_{i=1}^{n}(x_i - \bar{x})^3}{\left[\frac{1}{n}\sum_{i=1}^{n}(x_i - \bar{x})^2\right]^{3/2}}$$

where $x_i$ is the ith sample of the signal and $$\bar{x} = \frac{1}{n}\sum_{i=1}^{n}x_i$$

is the sample mean of the n samples.

2. A usual skewness estimator in accordance with $$\frac{\sqrt{n(n-1)}}{n-2}\frac{\kappa_3}{\kappa_2^{3/2}}$$

where $\kappa_j$ is symmetric, unbiased estimator of the jth cumulant.

3. A Pearson mode skewness in accordance with $$\frac{\bar{x} - \hat{x}}{\sigma}$$

where $\hat{x}$ is the mode of the samples and $$\sigma = \sqrt{\frac{1}{n}\sum_{i=1}^{n}(x_i - \bar{x})^2}.$$

4. A Pearson's second skewness coefficient in accordance with $$\frac{\bar{x} - \tilde{x}}{\sigma}$$

where $\tilde{x}$ is the median of the samples.

5. A Bowley skewness in accordance with $$\frac{(Q_3 - Q_2) - (Q_2 - Q_1)}{Q_3 - Q_1}$$

where $Q_i$ is the ith interquartile range.

In an embodiment, a skewness value of a signal may be based at least in part on any of a number of multivariate skewness metrics, including, for example, metrics based at least in part on joint moments of an underlying multivariate signal, projections of the underlying multivariate signal onto a line, volumes of simplices within the multivariate space, or any combination thereof.

In addition to the skewness metrics described above, embodiments described herein may include any signal metric that measures the asymmetry of a signal around its mean or average value. In an embodiment, the skewness metric may be based at least in part on any one or more of the following:
1. The ratio of the area under the positive portion of a pulse of the received first signal to the area under the negative portion of the same pulse.
2. The ratio of the positive peak of a pulse of the time derivative of the received first signal to the negative peak of the same pulse.
3. The ratio of the duration of the upstroke of a pulse of the received first signal to the duration of the downstroke of the same pulse.

In some embodiments, a skewness value of a signal may be based at least in part on a constant multiple of any skewness metric. It will be understood that the foregoing are merely examples of techniques for calculating a skewness value in accordance with the methods and systems described herein.

In an embodiment, the patient monitoring system may be a CNIBP system that provides blood pressure readings based at least in part on measurements of a differential pulse transit time (DPTT) detected via two or more sensors. The skewness of the signals transmitted by the two or more sensors may be compared and tracked over time, for example, by comparing the ratio of skewness values at times T1 and T2 as described above with reference to processor 500. Changes in patient medical status (e.g., when a patient undergoes a seizure or arrest) may result in different changes in the shapes of the waveforms transmitted by the two or more sensors. Such changes may be detected as a change between the first and second ratio, and such a change may be quantified by a first skewness value for determining whether a recalibration is necessary.

At step 606, an electronic recalibration signal may be generated based at least in part on a comparison of the first skewness value and a reference skewness value. This comparison may include a threshold test, for example, as described above with reference to step 506 of process 500. In an embodiment, the reference skewness value is based at least in part on past values of the electronic recalibration signal, associated skewness values or any combination thereof. For example, an electronic recalibration signal may be generated based at least in part on whether the first skewness value falls outside a range centered at a reference skewness value. The reference skewness value may be the average of the skewness metric applied to a fixed number of past time windows and the range may include a band of values centered on the average (e.g., a multiple of standard deviations). In the DPTT measurement example described above, the absolute difference between the first and second ratios may be compared against a single threshold to determine whether the change exceeds this threshold, which may signal a need to initiate a recalibration. In an embodiment, the electronic recalibration signal may be further based at least in part on a measurement quality signal (e.g., as described above with reference to process 500). For example, low quality measurements may indicate that a patient is moving or that a sensor has malfunctioned, in which case a recalibration should be delayed until a higher quality measurement can be obtained. Such an embodiment may advantageously reduce time and resources devoted to wasteful recalibrations in periods of low signal quality.

At step 608, a recalibration of the measurement device may be initiated based at least in part on the comparison of step 606. Initiating a recalibration may include transmitting an electronic recalibration signal to a calibration device 80 that includes a command to commence a recalibration process. In an embodiment, initiating a recalibration may include transmitting an electronic recalibration signal to a calibration device 80 that schedules a future recalibration process. In an embodiment, initiating a recalibration includes sending an electronic recalibration signal that includes a frequency at which calibration device 80 should perform upcoming calibrations. Such an embodiment may be advantageous when a patient is undergoing rapid changes in condition, as reflected in changes in the skewness values of the received first signal, and more frequent recalibrations are desired than when a patient is in a stable state. Additional details regarding various illustrative embodiments of the steps of process 600 are described below with reference to process 700.

Figure 7:
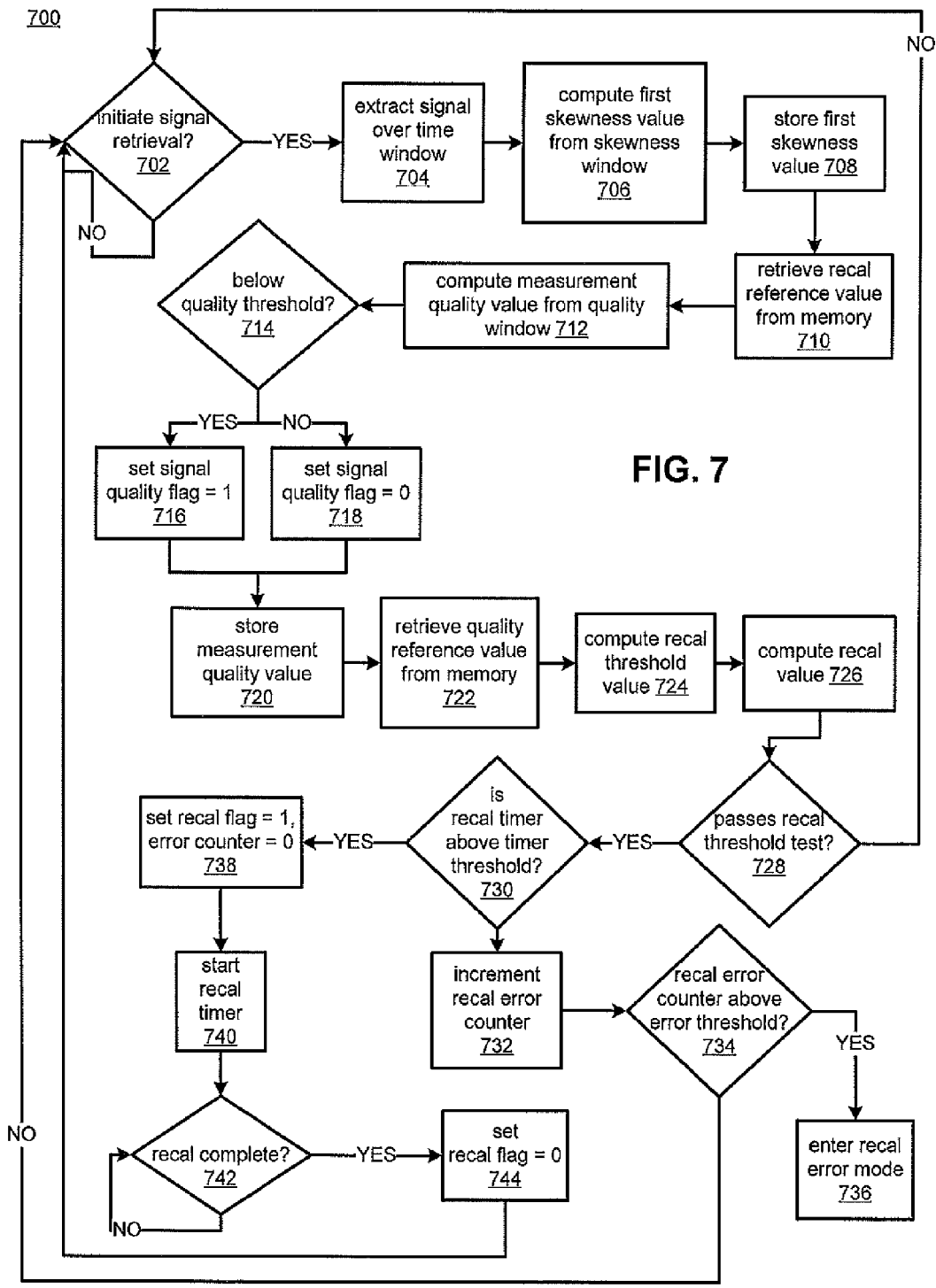

FIG. 7 is a flow diagram of an illustrative recalibration initiation process in accordance with an embodiment. For ease of presentation, process 700 will be described as performed by processor 312; however, it will be understood that process 700 may be performed by any suitable processing device communicatively coupled to monitor 14.

At step 702, processor 312 may determine whether to initiate retrieval of an electronic signal. Retrieval may be initiated according to a fixed monitoring schedule, or may be performed in response to a request indicated by a patient or care provider via user inputs 56, or both. At step 704, the electronic signal over a time window may be extracted. As described above with reference to processes 500 and 600, past values of the electronic signal may be extracted, and the width and delay of such a time window may vary. The electronic signal may be received at processor 312 in real-time (e.g., as signal 316), or may be extracted from a buffer such as QSM 74 or from RAM 54.

At step 706, processor 312 may calculate a first skewness value from the extracted signal over a skewness window. The skewness window may be a sub-window of the time window of step 704, and may represent a subset of the extracted signal data. The skewness value may be calculated in accordance with any of the embodiments described herein. At step 708, processor 312 may store the calculated first skewness value in one of more storage devices such as RAM 54. Processor 312 may store any of the calculated values described herein at a remote storage device, enabling other remote processing devices to access and analyze the stored calculated values.

At step 710, processor 312 may retrieve a recalibration reference value from a storage device (e.g., RAM 54). This recalibration reference value may be, for example, any of the reference values described above with reference to process 600, and may itself be a value previously calculated and stored by processor 312. At step 712, processor 312 may compute a measurement quality value of the signal extracted in step 704 over a quality window. The quality window may be a sub-window of the time window of step 704, and may represent a subset of the extracted signal data. In an embodiment, the quality window may be different from the skewness window. For example, a quality window may include the most recently received single pulse of a PPG signal, while the skewness window may include a sequence of several past pulses. For instance, a quality window may encompass from two to 10 pulses, and the quality threshold at step 714 may be derived at least in part from the standard deviation, or other measure of variability, of the skewness metrics for those pulses. In a further embodiment, the length of a quality window may be linked to the quality of the signal which it contains. For example, if the current signal quality is deemed to have low quality, then a longer twenty pulse window may be employed, while a signal having high quality may employ a window of shorter duration (e.g., one that is five pulses in duration).

Once the measurement quality value has been computed at step 712, processor 312 may compare the measurement quality value to a quality threshold at step 714. If the measurement quality value is below the threshold, processor 312 may set a signal quality flag to one at step 716 (i.e., as an indicator of low signal quality). Step 714 may include setting a signal quality variable equal to one in a memory (e.g., RAM 54). In an embodiment, the signal quality flag may be a "logic high" signal that may be passed directly to measurement quality output 324. Alternately, if processor 312 determines at step 714 that the measurement quality value is above the threshold, a signal quality flag may be set to zero at step 718.

After a signal quality flag has been set, processor 312 may proceed to step 720 and may store the measurement quality value, then may proceed to step 722 and may retrieve a quality reference value from a memory (e.g., RAM 54, or a remote storage). The stored measurement quality value may be used in later executions of process 700, or for additional calculations performed by processor 712 as described above. At step 724, processor 312 may computes a recalibration threshold value, which may be based at least in part on the measurement quality value and the quality reference value. For example, when the measurement quality value is lower than a baseline value, the recalibration threshold may be higher than a baseline value.

At step 726, processor 312 may compute a recalibration value based at least in part on the first skewness value calculated at step 708 and the recalibration reference value retrieved at step 710. Such a recalibration value may be computed in a manner similar to the electronic recalibration signal described above with reference to process 600. In an embodiment, step 726 may include computing an absolute difference between the first skewness value and the recalibration reference value, computing a relative and/or normalized difference, or a combination thereof.

At step 728, the recalibration value computed at step 726 may be subject to a recalibration threshold test to determine whether a recalibration procedure may be initiated. Illustrative examples of threshold tests are described in detail above. For example, step 728 may include determining whether the first skewness value falls in a range centered on the recalibration reference value. If the threshold test at step 728 is failed, processor 312 may not initiate a recalibration and may return to step 702 and may wait for an appropriate time to initiate signal retrieval.

If the threshold test at step 730 is passed, processor 312 may then compare the value of a recalibration timer to a timer threshold. The recalibration timer may be reset at the beginning of each recalibration procedure, and may count the time or clock cycles elapsed since the last recalibration. In an embodiment, a timer threshold may be fixed to represent a minimum delay between recalibrations in order to prevent the patient monitoring system from undergoing too many unnecessary recalibrations. If the recalibration timer has not exceeded the timer threshold at step 730, not enough time has passed since the last recalibration and processor 312 may record this event by incrementing a recalibration error counter at step 732.

Processor 312 may proceed from step 732 to step 734 and may compare the value of the recalibration error counter to a recalibration error threshold. In an embodiment, the recalibration error threshold may represent the maximum allowable number of "incomplete" recalibration attempts (e.g., the number of times processor 312 passes through steps 730 and 732) before an error mode may be entered. If the recalibration error counter exceeds the recalibration error threshold at step 734, the patient monitoring device may enter a recalibration error mode at step 736. This error mode may include any one of requiring a manual intervention by a user; requiring a electronic or remote restart of the device; requiring servicing by the device manufacturer; requiring an alternative recalibration procedure; performing a diagnostic of the monitoring operations; or any combination thereof.

Returning to step 730, if the recalibration timer exceeds the timer threshold, then sufficient time may have passed since the last recalibration to perform another recalibration. Processor 312 may then proceed to step 738 and may set a recalibration flag to one and may set an error counter to zero. Setting the recalibration flag to one may provide a signal to calibration device 80 to commence a recalibration of the device. Processor 312 may start the recalibration timer at step 740 (once the recalibration is initiated), then may proceed to step 742 and may wait until the recalibration is complete. Processor 312 may wait for a fixed period of time corresponding to a known recalibration interval, may receive a "recalibration complete" signal from calibration device 80, or a combination thereof.

Once the recalibration is complete, processor 312 may set the recalibration flag to zero at step 734 then may return to step 702 and may wait to initiate signal retrieval. In practice, one of more of the steps shown in processes 500, 600 and 700 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems and apparatuses, but is intended to include variations to and modifications thereof which are within the spirit of the following claims.

What is claimed is:

1. A method for initiating a recalibration of a measurement device, comprising:
   receiving a first sensor signal representative of a physiological process;
   calculating a skewness value representative of a skewness of the received first signal;
   generating, an electronic recalibration signal based at least in part on a comparison of the skewness value and at least one reference skewness value; and
   transmitting the electronic recalibration signal to a measurement device to initiate a recalibration of the measurement device.

2. The method of claim 1, wherein the received first signal is a photoplethysmograph signal.

3. The method of claim 1, wherein the measurement device is a part of a continuous, non-invasive blood pressure monitoring system.

4. The method of claim 1, wherein calculating a skewness value comprises calculating at least one of a skewness of a time derivative of the received first signal and a ratio of characteristics of the received first signal.

5. The method of claim 1, wherein the at least one reference skewness value is based at least in part on at least one past portion of the received first signal.

6. The method of claim 1, wherein the received first signal is based at least in part on a comparison of an electronic signal generated by a sensor located at a first site on a patient's body and an electronic signal generated by a sensor located at a second site on the patient's body.

7. The method of claim 1, further comprising:
generating an electronic measurement quality signal based at least in part on a comparison of the skewness value and the at least one reference skewness value.

8. The method of claim 7, wherein the electronic recalibration signal is further based at least in part on the electronic measurement quality signal.

9. The method of claim 7, further comprising determining, with the measurement device, a physiological measurement based at least in part on the received first signal and the electronic measurement quality signal.

10. A system for initiating a recalibration of a measurement device, comprising:
at least one memory device, storing at least one reference skewness value;
a calibration device, configured to initiate a recalibration of the measurement device in response to a recalibration signal;
a processor, communicably coupled to the at least one memory device and to the calibration device configured to receive a first sensor signal representative of a physiological process, the processor further configured to:
calculate a skewness value representative of a skewness of the received first signal;
retrieve the at least one reference skewness value from the at least one memory device;
generate a recalibration signal based at least in part on a comparison of the skewness value and the at least one reference skewness value; and
transmit the recalibration signal to the calibration device.

11. The system of claim 10, wherein the received first signal is a photoplethysmograph signal.

12. The system of claim 10, wherein the measurement device is a part of a continuous, non-invasive blood pressure monitoring system.

13. The system of claim 10, wherein calculating a skewness value comprises calculating at least one of a skewness of a time derivative of the received first signal and a ratio of characteristics of the received first signal.

14. The system of claim 10, wherein the at least one reference skewness value is based at least in part on at least one past portion of the received first signal.

15. The system of claim 10, wherein the received first signal is based at least in part on a comparison of a signal generated by a sensor located at a first site on a patient's body and a signal generated by a sensor located at a second site on the patient's body.

16. The system of claim 10, wherein the processor is further configured to:
generate a measurement quality signal based at least in part on a comparison of the skewness value and at least one reference skewness value.

17. The system of claim 16, wherein generating a recalibration signal is further based at least in part on the measurement quality signal.

18. The system of claim 16, wherein the processor is further configured to:
generate a physiological measurement based at least in part on the received first signal and the measurement quality signal.

19. A non-transitory computer-readable medium for use in initiating a recalibration of a physiological measurement, the computer-readable medium having computer program instructions recorded thereon for causing processing equipment to:
receive a first sensor signal representative of a physiological process;
calculate a skewness value representative of a skewness of the received first signal;
generate, an electronic recalibration signal based at least in part on a comparison of the skewness value and at least one reference skewness value; and
transmit the electronic recalibration signal to a measurement device to initiate a recalibration of the measurement device.

20. The non-transitory computer-readable medium of claim 19, wherein the received first signal is a photoplethysmograph signal.

* * * * *